United States Patent [19]

Yerlikaya et al.

[11] Patent Number: 5,256,155
[45] Date of Patent: Oct. 26, 1993

[54] DROP DETECTION METHOD AND APPARATUS

[75] Inventors: Denis Y. Yerlikaya, Des Peres; Randall J. Krohn, Ballwin, both of Mo.

[73] Assignee: Sherwood Medical Company, St. Louis, Mo.

[21] Appl. No.: 678,639

[22] Filed: Apr. 1, 1991

[51] Int. Cl.⁵ .............................................. A61M 5/00
[52] U.S. Cl. ................................. 604/246; 604/251; 604/67; 128/DIG. 13
[58] Field of Search .......................... 128/DIG. 13; 604/251–253, 65, 67, 245, 246; 377/21; 222/14, 17

[56] References Cited

U.S. PATENT DOCUMENTS

| | | | |
|---|---|---|---|
| 4,058,699 | 11/1977 | Van Vloten | 219/121 LM |
| 4,490,140 | 12/1984 | Carr et al. | 604/65 |
| 4,498,901 | 2/1985 | Finch | 604/65 |
| 4,533,350 | 8/1985 | Danby et al. | 604/253 |
| 4,680,462 | 7/1987 | Kamen | 604/253 |
| 4,718,896 | 1/1988 | Arndt et al. | 604/253 |
| 4,720,636 | 1/1988 | Benner, Jr. | 250/573 |
| 4,786,800 | 11/1988 | Kamen | 604/253 |
| 5,012,496 | 4/1991 | Weinreb et al. | 604/253 |

FOREIGN PATENT DOCUMENTS 0209659 1/1987 European Pat. Off. .
8603002 5/1986 PCT Int'l Appl. .

*Primary Examiner*—C. Fred Rosenbaum
*Assistant Examiner*—Manuel Mendez
*Attorney, Agent, or Firm*—Andrew J. Beck; Montgomery W. Smith; Curtis D. Kinghorn

[57] ABSTRACT

A drop detector circuit and method are provided for a drop detector of the type including a drop chamber and an electro-optical sensor. A photodiode detects drops passing through its optical sensing path, and a capacitor is connected between the photodiode and an amplifier to block the DC component of the diode signal. After amplification, the signal is passed through a low pass filter to further block signals caused by undesirable factors. The cutoff frequency of the low pass filter is controlled by a microprocessor that controls the pump that pumps liquid from the drop chamber.

13 Claims, 6 Drawing Sheets

DROP DETECTION METHOD AND APPARATUS

FIELD OF THE INVENTION

The invention relates generally to drop detection in a medical liquid drop chamber and, more specifically, concerns a drop detection method and apparatus for use in an ambulatory or household environment.

BACKGROUND OF THE INVENTION

Medical drop chambers are used in various medical devices for metering and monitoring the flow rate of a fluid being administered to a patient. In a given drop chamber, each drop has a uniform volume of fluid. Therefore, by counting the number of drops falling in a given time period, the flow rate can be calculated easily. Such drop chambers are used, for example, in gravity-driven or pump-driven infusion systems.

Devices are known in the art for automatically sensing the drops in a chamber. These may, for example, be connected to circuits that can compute and display the flow rate or to alarms that indicate when the flow rate is too high or too low. These drop detectors are often optical sensors that react to a drop breaking optical communication between a light source and a sensor. In a controlled environment, such as a hospital, few outside conditions affect the optical sensors. The ambient light is fairly uniform throughout the environment and the drop chamber is relatively immobile and usually kept upright.

However, in either an ambulatory or household environment, several factors that may affect the optical sensors must be handled properly by the drop sensor to avoid false readings or alarms. These factors include widely varying ambient light conditions and excessive movement and tilting of the drop chamber, especially in ambulatory situations. False readings caused by these factors are a major reason for physicians' reluctance to use the ambulatory devices. It has therefore been a goal in the art that the drop detectors be capable of increased sensitivity to the drops, while being immune to the ambient light variation or movement and change in orientation of the chamber.

U.S. Pat. No. 4,720,636 to Benner, Jr. discloses a drop detection structure and detection circuitry that includes two photodetectors, one for sensing a decrease in light caused by a drop passing in front of it, and another for detecting an increase in light caused when a drop passes nearby and reflects additional light. A drop would pass nearby, for example, if the chamber were tilted. However, in the event of a very high tilt angle, coherent drops are not always formed. The liquid may enter the chamber and immediately spread onto the interior surface of the chamber, rather than falling to the bottom of the chamber U.S. Pat. No. 4,718,896 to Arndt et al. discloses a drop detector that includes an array of light emitter/sensor pairs arranged to detect drops falling at angles of up to 30 degrees from the normal, vertical orientation. Tilt angles greater than 30 degrees are found in everyday use of the medical devices containing these detectors, rendering the detectors of this patent only partially effective.

It is thus an object of the invention to provide an improved drop detector for a liquid drop chamber which is capable of detecting drops in a variety of conditions and applications, without causing false readouts or alarms.

It is a further object of the invention to provide an improved drop detector that is immune to changes in ambient light.

It is a further object of the invention to provide an improved drop detector that can detect drops at tilt angles of up to 80 degrees from the normal, vertical positioning of the drop chamber.

It is a still further object of the invention that the improved drop detector be constructed of readily available components and be cost-efficient and relatively inexpensive to manufacture.

In accordance with the invention, a drop detector circuit is provided that includes a rectangular photodiode for detecting drops passing by its optical sensing path, and a DC signal blocking element, preferably a capacitor, is electrically interposed between the photodiode and amplifiers to block amplification of signals caused by ambient light. After amplification, the signals are passed through a low pass filter and a differentiator circuit to further block signals caused by undesirable factors.

The foregoing and other objects and advantages of this invention will be appreciated more fully upon reading the following detailed description of a preferred embodiment in conjunction with the appended drawings.

BRIEF DESCRIPTION OF THE DRAWINGS

The preferred embodiments of the invention are described herein with reference to the appended drawings, wherein.

DETAILED DESCRIPTION OF THE PREFERRED EMBODIMENTS

Figure 1:
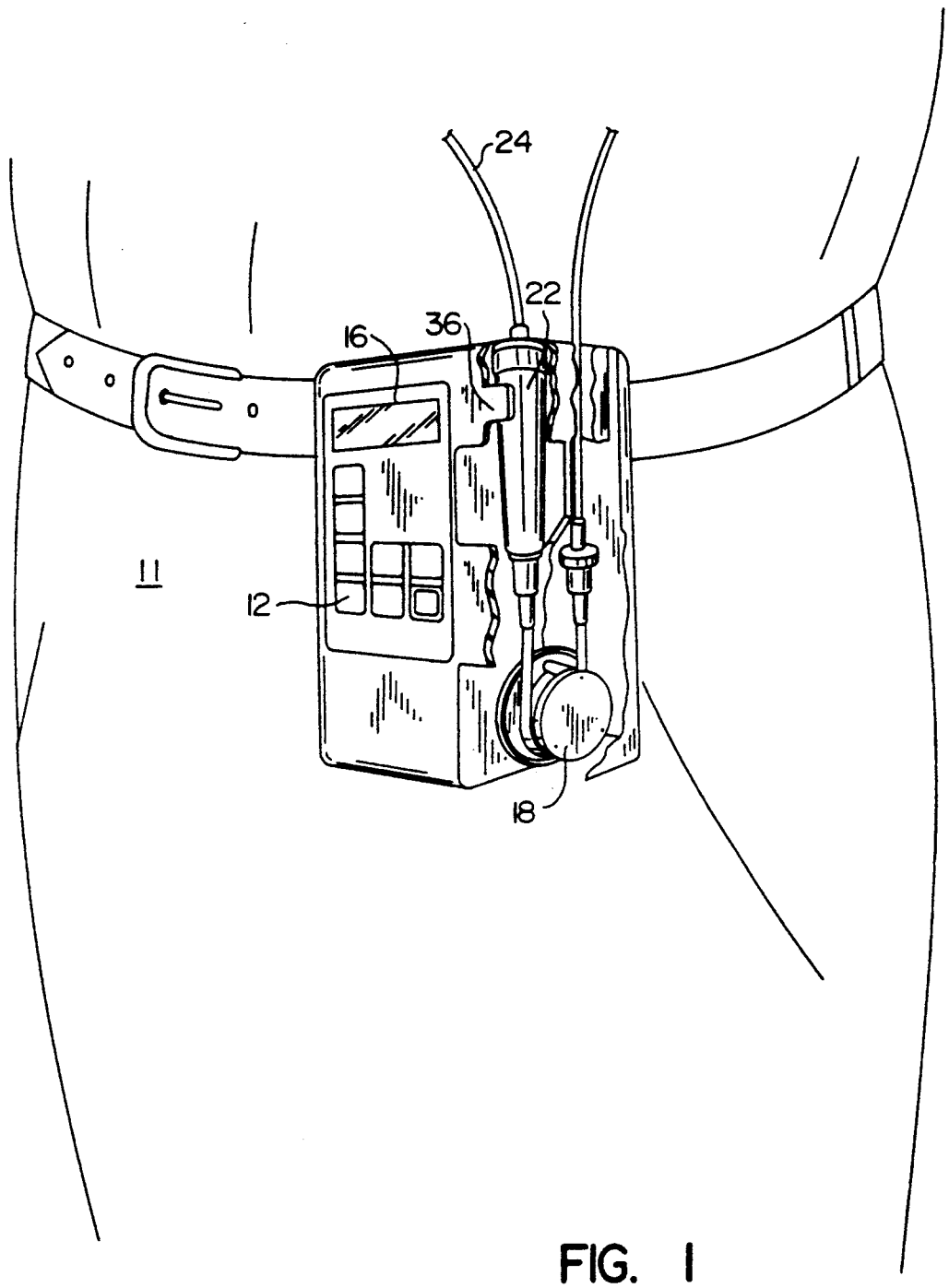
FIG. 1 is a perspective view illustrating the manner in which an ambulatory patient could use a drop detection apparatus embodying the invention.

In FIG. 1, a medical infusion device worn by a patient is generally designated by the reference numeral 10. The infusion device includes a pump for the enteral administration of fluids. It is to be understood that while the preferred embodiment is shown for a medical infusion device, the invention can be similarly used with any device making use of a drop chamber.

As can be seen in FIG. 1, the device is capable of being attached to the belt of a patient 11 in use, while the patient 11 is completely ambulatory. The device is thus subjected to significant tilting, jarring, and accelerations that must be accurately compensated for in the internal mechanisms and circuits of the device 10.

Figure 2:
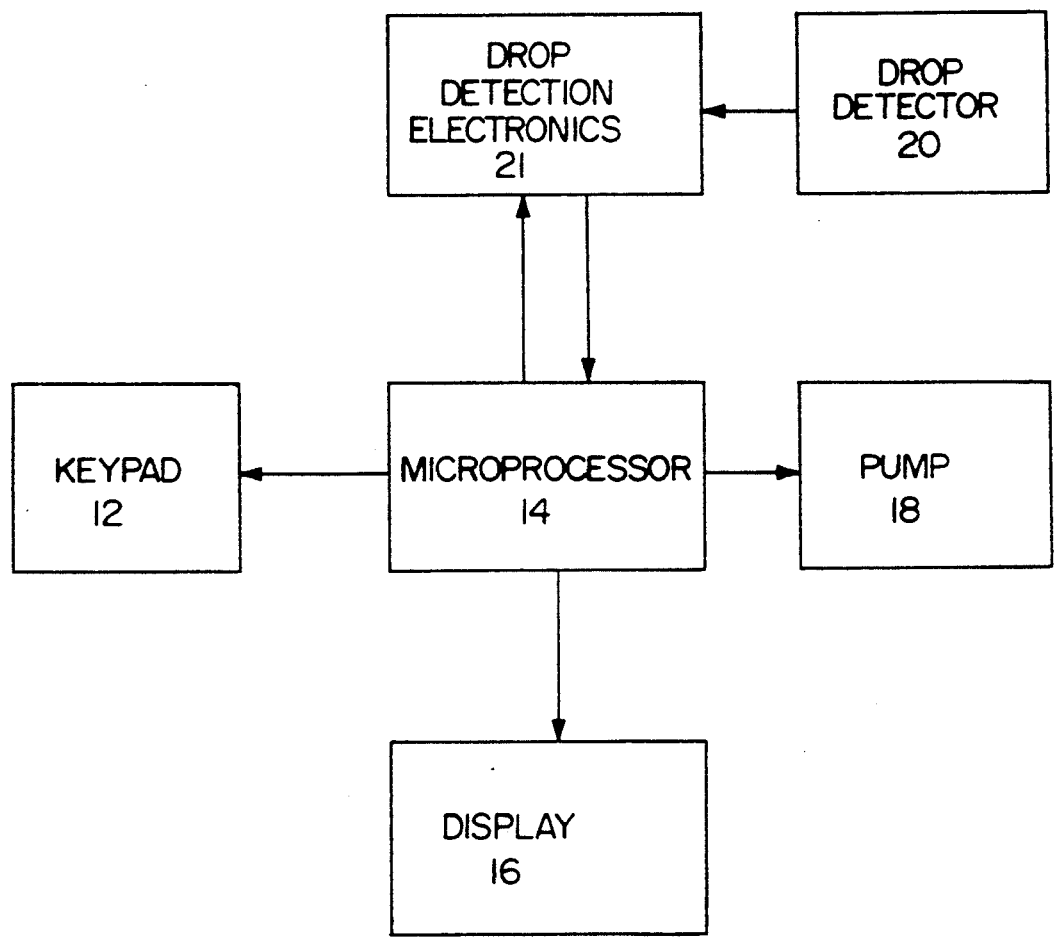
FIG. 2 is a functional block diagram of a drop detection apparatus embodying the invention.

The block diagram of FIG. 2 represents the electrical interaction of the major electronic and electromechanical components of the device 10 and shows signal connections. A keypad 12 allows operator input of device parameters, such as fluid flow rate, which are sent to a microprocessor 14. The microprocessor 14, in turn, provides information to the patient on a display 16 and controls a motor-driven pump 18. Drop detector 20, described in detail below, has a drop chamber which is interposed in the fluid flow path between a fluid supply (not shown) and the pump 18. A sensor monitoring the drop chamber detects the flow of fluid through the drop chamber and sends corresponding signals to drop detection electronics 21. The electronics 21 filter unwanted components in the signals from the detector 20 and pass the remainder to the microprocessor 14. The microprocessor 14 also returns control signals to the electronics 21, as described below.

In operation, the pump 18 feeds fluid for the patient at a rate set into the device by means of the keypad 12 and maintained by the microprocessor 14. All of the fluid that the pump 18 feeds to the patient 11 must pass through a drop chamber and no dripping occurs if the pump stops feeding fluid. Since the fluid can pass through the drop chamber only in the form of drops of fixed volume, the drop count is therefore an extremely accurate measure of the quantity of fluid supplied to the patient. Accurate drop detection therefore permits accurate metering of fluid flow and accurate control of the pump by the microprocessor 14.

Figure 4:
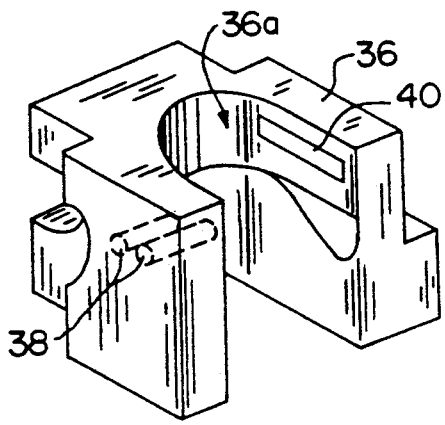
FIG. 4 is a perspective view of a portion of the infusion device, showing a mounting receptacle for a drop detector assembly.

Drop detector 20 includes a yoke 36 (see FIG. 4), which is mounted on device 10 and a drop chamber 22 (see FIG. 5), which is removably received within yoke 36, thus supporting the drop chamber 22 in the infusion device 10. Yoke 36 has a passageway 36a, which receives drop chamber 22 in an upright position. Two infrared light emitting diodes 38, preferably Seimens SFH 485-2 IRLEDs 38 are mounted side-by-side, so as to face into passageway 36a and drop chamber 22. Diodes 38 are preferably directed along lines intersecting the axis of the drop chamber 22 and form an angle of 20 degrees. They are also preferably offset from the top of the drop chamber 22 by one-third of its height.

Figure 5:
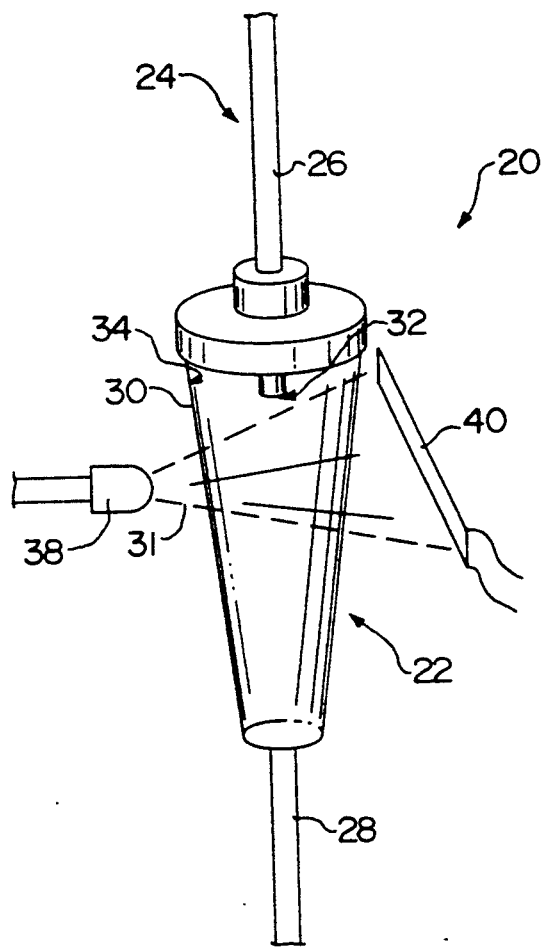
FIG. 5 is a perspective view of a drop chamber and drop detector assembly, showing the optical path coverage of the drop detector.

FIG. 5 illustrates the removable drop chamber 22, connected in series with and interrupting a delivery tube 24 that runs from a fluid source (not shown) to a patient (11 in FIG. 1). Fluid enters the drop chamber 22 from the top portion 26 of the tube 24 as shown in FIG. 5 and exits the chamber 22 through the bottom portion 28. The drop chamber 22 is a sealed unit, except for the entrance and exit portions 26,28 of the tube 24, which penetrate the top and bottom of the chamber 22, respectively. The chamber 22 has a generally frusto-conical light-transmissive sidewall 30, with the smaller diameter at its bottom. The top portion 26 of the tube 24 extends partially into the chamber 22, creating a drop formation area 32. Fluid accumulates at this area 32, until it forms a complete drop, which then falls to the bottom of the chamber 22.

When the chamber 22 is tilted, as often happens when the infusion device 10 is used in an ambulatory manner shown in FIG. 1, the drops will not fall to the bottom of the chamber 22, but will fall onto the side of the sloped sidewall 30 of the chamber 22. The tilt angle determines where the drop will hit the sidewall 30. At tilt angles above 70 degrees from vertical, the drops do not even fall, but tend to form a puddle on the sidewall 30 at position 34.

Mounted within the yoke 36 on the opposite side of the drop chamber 22 from the IRLEDs 38 is a rectangular photodiode 40, preferably a Vactec VTS 3092 photodiode, measuring 0.6 by 0.1 inches. It is mounted with its length parallel to the horizontal plane. The result of having two IRLEDs 38 opposite a single photodiode 40 is to create a triangular optical path 41 that can be broken by a drop passing through any portion of the horizontal cross section of the chamber 22 (as shown in FIG. 5). If a drop contacts the sidewall 30 of the chamber 22 and then slides down the wall 30, regardless of which side it travels on, the drop will pass through the optical path between the two IRLEDs 38 and the photodiode 40. Because the yoke 36 that holds the drop chamber 22 and the photodiode 40 is not sealed (as the drop chamber 22 and tube 24 are removable), ambient light is constantly detected by the photodiode 40, as well as light from the IRLEDs 38. This will be discussed in greater detail below.

With a high tilt angle of the drop chamber 22 and varying ambient light conditions, the changes in light actually caused by drops can be relatively small and difficult to detect with the photodiode 40. To compensate for these conditions, the photodiode 40 is preferably connected to a drop detection circuit 41, schematically illustrated in FIG. 3. The drop detection circuit filters out any unwanted portions of the signal from the photodiode 40 and amplifies the remainder of the signal, which is presumably caused by drop flow. The microprocessor 14 processes the output signal from the circuit 41 to determine if proper flow is occurring and control pump 18 and display 16 accordingly.

Figure 3:
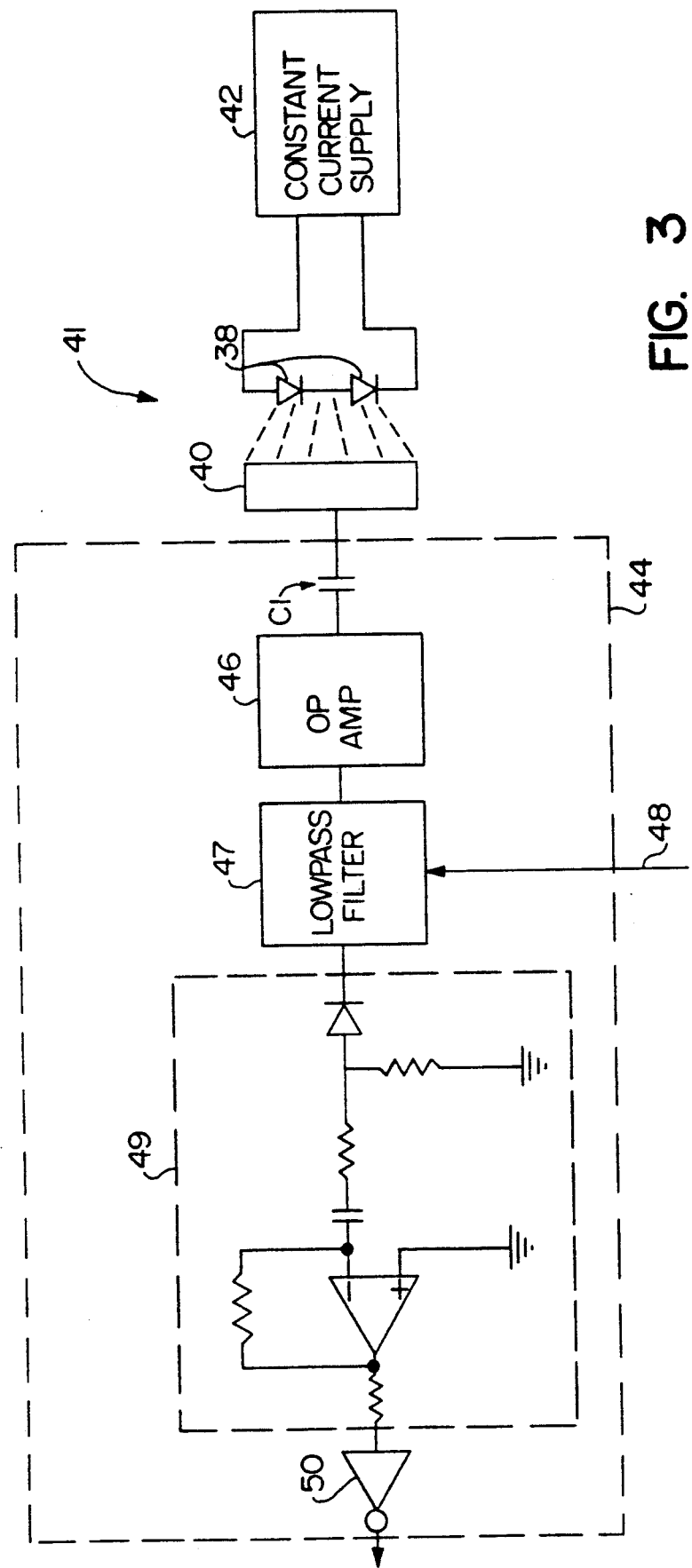
FIG. 3 is a circuit schematic diagram showing a drop detection circuit according to invention.

The drop detection circuit 41 shown in FIG. 3 includes a driver circuit 42 that powers the two IRLEDs 38 and preferably provides a constant current supply to the IRLEDs 38 to maintain constant optical output. Any variation in the optical output would add unwanted signals to the photodiode 40, so constant optical output is important. A detector circuit 44 receives electrical signals from the photodiode 40 and converts them to a signal indicating whether or not a drop is flowing.

The detector circuit 44 includes an operational amplifier 46, which amplifies the signal from the photodiode 40, after which it is applied to a lowpass filter 47. Filter 47 is a switched capacitor lowpass filter, preferably a National Semiconductor Corporation LMF60-100. It filters out any components of the signal above a nominal cut-off frequency that is determined by an input clock signal 48 from the microprocessor 14 of the infusion device 10.

The drop rate is directly proportional to the speed of the pump motor, which is constant and controlled by the microprocessor. The flow rate (i.e. number of drops per unit time) is varied by starting and stopping the pump motor for different time periods. The microprocessor thus produces a filter clock signal 48 to control the cut-off frequency of the filter 47, based on this known speed and drop rate. In the preferred embodiment, the filter clock is at 350 Hz, and filter 47 is designed to divide the filter clock by 100 to derive a cutoff frequency of 3.5 hz.

Connected in series between the photodiode 40 and lowpass filter 47 is a capacitor C1. This capacitor blocks the DC component of the voltage produced by the photodiode 40, which is typically developed in response to the ambient light level. Only variable signals, such as those caused by drops, are passed to the filter 47. Some changes in ambient light may also produce signals that will pass through the capacitor to the filter 47. However, the cutoff frequency determined by the microprocessor tends to limit the filter's passband narrowly to only signals produced by drops.

Blocking the DC component of the signal from photodiode 40 also allows the relatively weak signals from the photodiode to be amplified with a much higher gain than would normally be possible. If the gain of the operational amplifier 46 in filter 47 (approximately 70) were applied to the signals of conventional drop photodetectors, the amplifier 46 would saturate.

Figure 6:
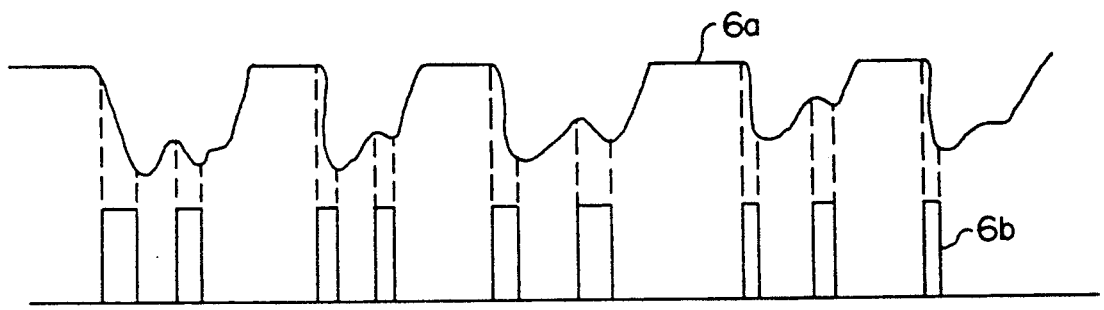
FIG. 6 is a waveform diagram representing typical input and output of a portion of a circuit as in FIG. 3.

After amplification and filtering, the signals are passed through a differentiator circuit 49. The effect of this circuit 49 on the signals is illustrated in FIG. 6, wherein the upper waveform 6a represents typical output of the lowpass filter 47, which is input to the circuit 49, and lower waveform 6b represents the output of the circuit 49. As can be seen in FIG. 6, the circuit outputs a positive pulse in response to a negative slope of waveform 6a, preferably a slope greater than 0.3 volts per second, which has been found to be a reliable indicator of drop flow. The duration of the positive pulse equals the duration of the negative slope of waveform 6a.

Figure 7:
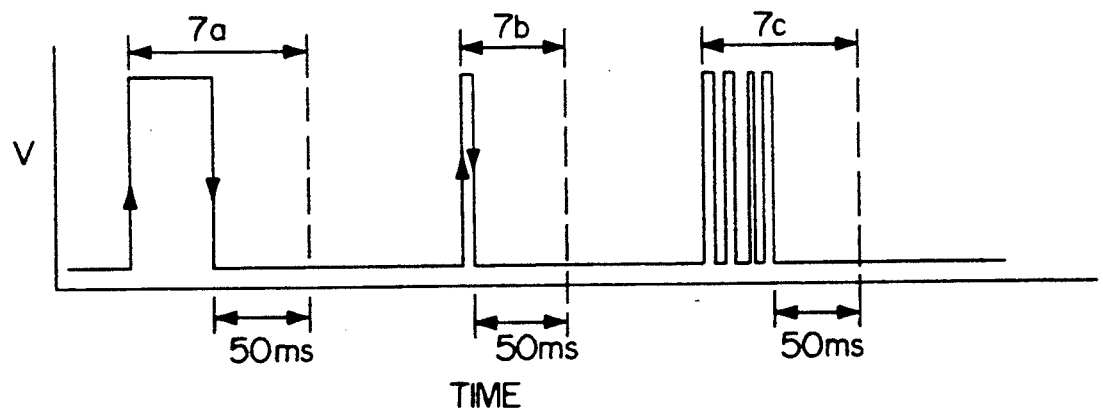
FIG. 7 illustrates typical output waveforms of a circuit as in FIG. 3.

The signals are then passed through logic invertor 50 and on to the microprocessor 14. For the microprocessor 14 to consider signals from the drop detection circuit 44 as representing a valid drop, there must be a rising edge, a falling edge and a subsequent minimal hold time, preferably 50 milliseconds. As seen in FIG. 7, at least three different types of inputs from the drop detection circuit 44 to the microprocessor 14 will result in a valid drop being detected.

In waveform 7a of FIG. 7, a long positive pulse is followed by the necessary hold time. This can occur when the drop chamber 22 is tilted at a high angle and a drop slides down the side of the drop chamber 22 past the photodiode more slowly than if it had fallen to the bottom of the chamber 22.

In waveform 7b of FIG. 7, a narrow positive pulse is followed by the requisite hold time. This represents a drop passing quickly past the photodiode, such as when the chamber 22 is in its proper vertical position.

In waveform 7c of FIG. 7, several narrow positive pulses are followed by the requisite hold time. This can represent any of various conditions, one of which is a drop bounding from excessive agitation of the infusion device 10.

Figure 8:
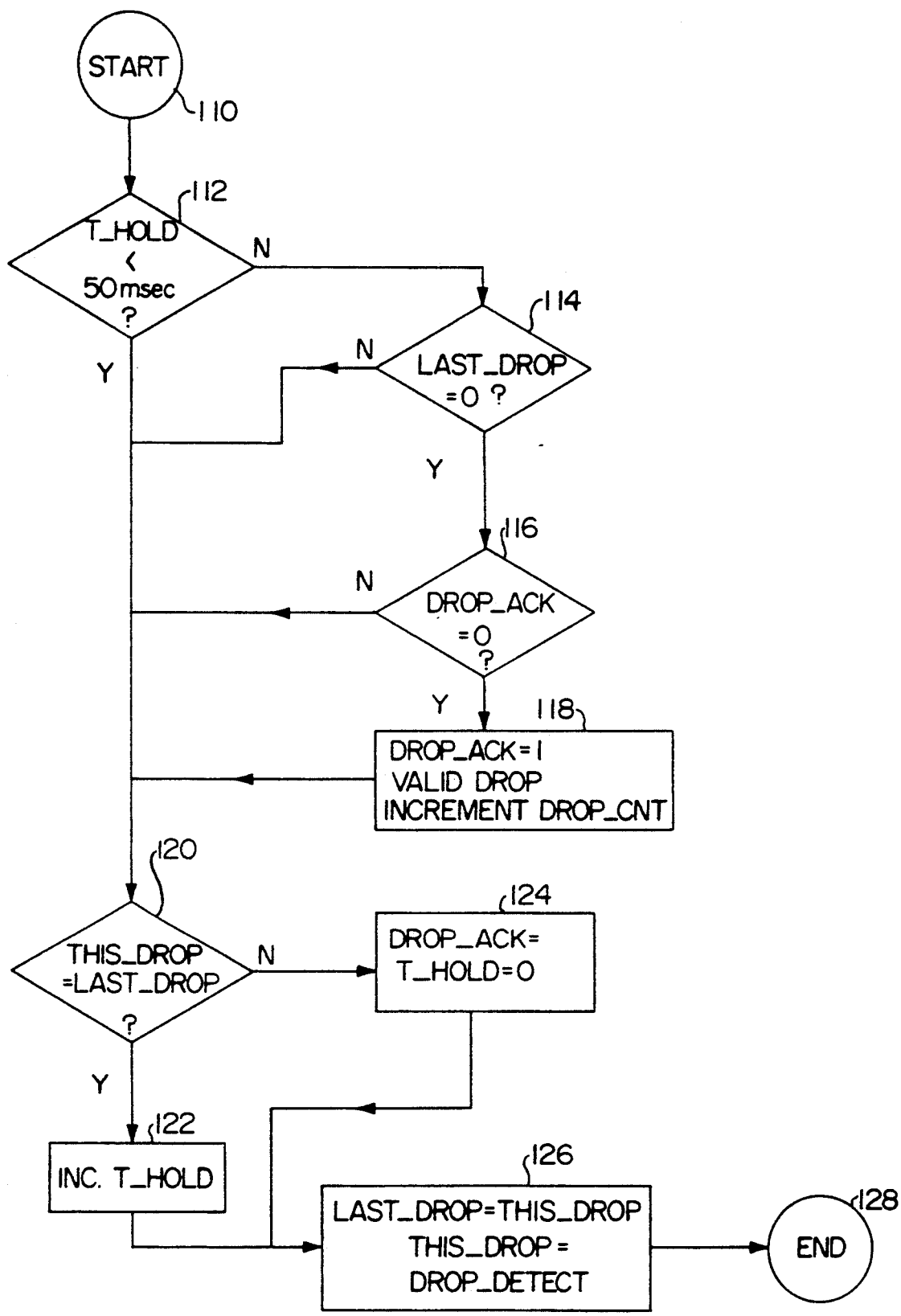
FIG. 8 is a flowchart representing the drop discrimination process utilized in an apparatus embodying the invention.

FIG. 8 is a flowchart representing the process performed by microprocessor 14 to determine if a valid drop has occurred, based upon signals such as those illustrated in FIG. 7. Processor 14 performs this routine every 1.36 msec. on an interrupt basis. The microprocessor 14 makes use of three software flags to keep track of the transitions in the signal received from drop detection electronics 21. The flag DROP$_{13}$ ACK is raised upon the occurrence of a negative transition if not previously set. The second and third flags reflect past states of DROP_DETECT the bit in microprocessor 14 memory that shows the status of drop detection electronics 21. Flag LAST_DROP shows the status of DROP_DETECT at the end of the previous iteration; flag THIS_DROP shows that status of DROP_DETECT at the end of the current iteration.

Referring to the flowchart of FIG. 8, the present routine is entered at block 110. Timer T_HOLD is tested at block 112 to determine if 50 msec has passed since the last transition of DROP_DETECT. If 50 msec has passed, the software tests LAST_DROP in block 114 to get the status of DROP_DETECT in the previous iteration, otherwise execution passes to block 120. If LAST_DROP is low at block 114, DROP_ACK is tested in block 118, otherwise execution passes to block 120. If DROP_ACK is high at block 118, execution passes to block 120. This signifies that the drop has already been acknowledged and counted by the microprocessor 14, as will be seen below.

Flags THIS_DROP and LAST_DROP are compared at block 120. If they are not equal, a transition of DROP_DETECT has occurred, and DROP_ACK and T_HOLD are reset at block 124, and execution passes to block 126; if they are equal, T_HOLD is incremented, and execution continues at block 126.

At block 126, LAST_DROP is set equal to THIS_DROP and then THIS_DROP is set equal to DROP_DETECT. The routine then ends at block 128.

It should be appreciated that, in operation, it will require many passes through the process illustrated in FIG. 8 to detect the occurrence of a valid drop. For example, should waveform 7a of FIG. 7 be encountered, DROP_ACK will be set to 1 at block 118 upon the occurrence of a negative-going transition followed by a 50 msec hold. Thereafter, blocks 112, 120, 122 and 126 are performed in repeated sequential passes until a positive transition is seen by block 120. In the next pass through the routine, blocks 112, 120, 122 or 124, and 126 are performed until T_HOLD exceeds 50 msec. At this point, a valid drop is detected, and DROP_ACK is set until the next transition of DROP_DETECT.

When a waveform such as waveform 7b in FIG. 7 is encountered, it is handled in precisely the same manner as just described, except that the negative transition is detected much sooner than it was with respect to waveform 7a.

Should a signal such as waveform 7c be encountered, the initial positive- and negative-going transitions are handled in the same manner as they were from waveform 7a. Whenever a transition occurs in DROP_DETECT as tested in block 120, T-HOLD and DROP_ACK are reset in block 124. This action will continue until no transitions are detected within a 50 msec window. The state of LAST_DROP is then tested in block 114; if low, DROP_ACK is tested in block 116. If DROP_ACK is low, a valid drop is counted by the microprocessor 14 and DROP_ACK is set in block 118.

From the above description of the preferred embodiments, it can be seen that the effect of movement and tilting of the drop chamber 22 on the output of the detection electronics is eliminated, while the effect of changes in ambient light are minimized. As a result, a drop chamber 22 may be accurately monitored in an ambulatory and changing environment.

While the disclosed embodiment of the invention is fully capable of achieving the results desired, it is to be understood that this embodiment has been shown and described for purposes of illustration only and not for purposes of limitation. Moreover, those skilled in the art will appreciate that many additions, modifications and substitutions are possible without departing from the scope and spirit of the invention as defined by the accompanying claims.

What is claimed is:

1. In a drop flow detector of the type including a drop chamber, a light source for passing light through said chamber, and a light detector responsive to said light after it has passed through said chamber for producing an electrical output signal related thereto, and circuit means responsive to the output signal of said light detector for determining the existence of drop flow, the improvement comprising:

blocking means for blocking the DC component of the output signal of said light detector from transmission to said circuit means; to produce a filtered output signal;

means for amplifying said filtered output signal, said amplifying means having a predefined saturation level, the filtered output signal being amplified by said amplifying means to a level that does not saturate the same, said level of amplification being substantially higher than the highest level of amplification which would not produce saturation if said DC component were present; means for generating a control signal, and, lowpass filtering means for blocking frequency components in said light detector output signal having a frequency above a cutoff frequency, said low pass filtering means located between said light detector and said circuit means, said cutoff frequency being variable in response to said control signal, said filtering means having a control input for receiving said control signal which determines said cutoff frequency.

2. A detector in accordance with claim 1, wherein said lowpass filtering means is a switched capacitor type filter.

3. A detector in accordance with claim 1 further including a motorized pump and a microprocessor for controlling the speed of said pump, said microprocessor also deriving said control signal related to said speed, said control signal being applied to said lowpass filtering means control input.

4. A detector in accordance with claim 3 wherein said cutoff frequency is approximately 4 Hz.

5. A detector in accordance with claim 1, wherein said blocking means comprises a capacitor electrically in series between said light detector and said circuit means.

6. A method for operating a drop flow detector of the type including a drop chamber, a light source for passing light through said chamber, a light detector, responsive to said light after it has passed through said chamber, for producing an electrical output signal related thereto, and circuit means responsive to the output signal of said light detector for determining the existence of drop flow, said circuit means including an amplifier having a predefined saturation level, said method comprising:

blocking the DC component of the output signal of said light detector from transmission to said amplifier to produce a filtered output signal;

amplifying the filtered output signal to a level that does not saturate the amplifier, said level of amplification being substantially higher than the highest level of amplification which would not produce saturation if said DC component were present: and, the step of generating a control signal;

filtering said filtered output signal with a lowpass filtering means having a variable cutoff frequency determined by a control signal, said lowpass filtering means connected between the light detector and the circuit means.

7. A method in accordance with claim 6, utilized in a system including a motorized pump and a microprocessor for controlling the speed of said pump, further comprising the step of said microprocessor producing said control signal related to said speed, 8. A method in accordance with claim 6, wherein said blocking step is accomplished by a capacitor connected electrically in series between said light detector and said circuit means.

9. A drop flow detector comprising:
a) a drop chamber;
b) light source for passing light through said drop chamber;
c) a light detector responsive to said light after it has passed through said drop chamber for producing an electrical output signal related thereto;
d) circuit means, responsive to the output signal of said light detector, for determining the existence of drop flow;
e) means for blocking the DC component of the output signal of said light detector of transmission to said circuit means;
f) means for generating a control signal; and,
g) lowpass filtering means for blocking frequency components in said light detector output signal having a frequency above a cutoff frequency, said low pass filtering means located between the light detector and said circuit means, said filtering means having a control input for receiving said control signal which determined said cutoff frequency.

10. A detector in accordance with claim 9 further including a motorized pump and a microprocessor for controlling the speed of said pump, said microprocessor also producing said control signal related to said speed, said control signal being applied to said lowpass filtering means control input.

11. A method in accordance with claim 6 further comprising the step of differentiating said output signal.

12. A method in accordance with claim 11 further comprising the steps of:
a) detecting a change in the differentiated output signal corresponding in kind to the change produced by a drop passing through the drop chamber between the light source and the light detector;
b) timing the time between the detected changes in the differentiated output signal corresponding in king to the change produced by a drop passing through the drop chamber between the light source and the light detector;
c) producing a second control signal in response to the time between the detected changes in the differentiated output signal corresponding in kind to the change produced by a drop passing through the drop chamber between the light source and the light detector being larger than a predetermined time, the second control signal indicating that a drop has passed through the drop chamber between the light source and the light detector.

13. A method in accordance with claim 12 wherein said predetermined time is about 50 milliseconds.

* * * * *